United States Patent [19]
Durant et al.

[11] 3,953,460
[45] Apr. 27, 1976

[54] ETHYLENE DERIVATIVES

[75] Inventors: Graham John Durant, Welwyn Garden City; John Colin Emmett, Codicote; Charon Robin Ganellin, Welwyn Garden City; Hunter Douglas Prain, Hitchin, all of England

[73] Assignee: Smith Kline & French Laboratories Limited, Welwyn Garden City, England

[22] Filed: May 9, 1974

[21] Appl. No.: 468,617

[30] Foreign Application Priority Data
May 17, 1973 United Kingdom............... 23568/73

[52] U.S. Cl. ................. 260/294.8 G; 260/294.8 F; 260/294.9; 260/296 R; 260/302 A; 260/302 D; 260/302 R; 260/307 R; 260/307 H; 260/308 R; 424/263; 424/272; 424/273; 424/275

[51] Int. Cl.$^2$......................................... C07D 213/28
[58] Field of Search....... 260/294.8 G, 309, 294.8 F

[56] References Cited
UNITED STATES PATENTS

| | | | |
|---|---|---|---|
| 3,734,924 | 5/1973 | Black et al............................ | 260/309 |
| 3,736,331 | 5/1973 | Black et al............................ | 260/309 |
| 3,808,336 | 4/1974 | Durant et al.......................... | 260/309 |
| 3,876,647 | 4/1975 | Durant et al................. | 260/294.8 G |
| 3,905,984 | 9/1975 | Durant et al................. | 260/294.8 H |

*Primary Examiner*—Alan L. Rotman
*Attorney, Agent, or Firm*—Joan S. Keps; Richard D. Foggio; William H. Edgerton

[57] ABSTRACT

The compounds are ethylene derivatives which are inhibitors of histamine activity, in particular, inhibitors of H-2 histamine receptors. A compound of this invention is 1-nitro-2-methylamino-2-[2-((4-methyl-5-imidazolyl) methylthio)ethylamino]-ethylene.

7 Claims, No Drawings

ETHYLENE DERIVATIVES

This invention relates to ethylene derivatives, in particular to pharmacologically active 1,1-diaminoethylene derivatives, and to processes for their preparation. These compounds are inhibitors of H-2 histamine receptors. In addition, this invention relates to pharmaceutical compositions comprising these compounds and to methods of inhibiting H-2 histamine receptors with these compounds. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involved a receptor which has been designated as H-1. A further group of substances has been described by Black et al. (Nature 1972, 236, 385) which are distinguished by the fact that they act at histamine receptors other than the H-1 receptor and these other receptors have been designated as H-2 receptors. This latter group of substances, to certain of which the present invention relates, are thus of utility in inhibiting certain actions of histamine which are not inhibited by the above-mentioned "antihistamines", that is they are H-2 histamine receptor inhibitors. Inhibitors of H-2 histamine receptors are useful, for example, as inhibitors of gastric acid secretion. The substances of this invention may also be of utility as inhibitors of certain actions of gastrin.

The 1,1-diaminoethylene derivatives with which the present invention is concerned may be represented by the following general formula:

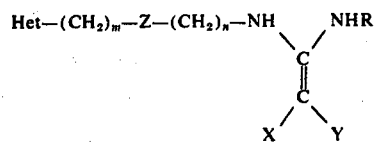

FORMULA 1 wherein X and Y, which may be the same or different, are hydrogen, nitro, cyano or $SO_2Ar$ but are not both hydrogen; R is hydrogen, lower alkyl such as methyl or Het $(CH_2)_mZ(CH_2)_n$; Z is sulphur or methylene; $m$ is 0, 1 or 2 and $n$ is 2 or 3 provided that the sum of $m$ and $n$ is 3 or 4; Het is a nitrogen containing 5 or 6 membered heterocyclic ring such as imidazole, pyridine, thiazole, isothiazole, oxazole, isoxazole, triazole or thiadiazole which ring is optionally substituted by lower alkyl, hydroxyl, halogen or amino; and Ar is an aryl group such as phenyl optionally substituted by halogen, methyl or amino, or a pharmaceutically acceptable acid addition salt thereof.

It will be appreciated, in the case where R is Het $(CH_2)_mZ(CH_2)_n$, that Het, $m$, $n$, and Z need not have the identical significance as in the other part of the formula.

Throughout the present specification, by the term "lower alkyl" we mean an alkyl group containing from 1 to 4 carbon atoms.

It will be understood that the structure illustrated in Formula 1 and in Formula I (a) below, is only one of several representations and that other tautomeric forms as shown in Formulae II and III and the other geometrical isomer shown in Formula IV are also covered by the present invention. In Formula II to IV and I (a) $R^1$ represents Het—$(CH_2)_m$—$Z(CH_2)_n$.

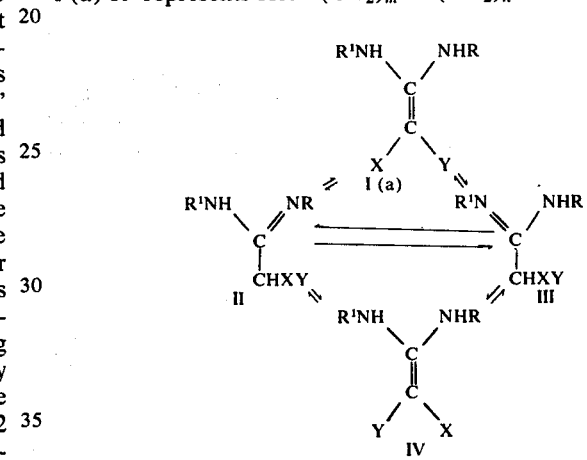

In a preferred group of compounds of formula I R is methyl or Het $CH_2SCH_2CH_2$, Z is sulphur, $m$ is 1 and $n$ is 2. Most suitably Het is imidazole, thiazole, isothiazole or pyridine and is optionally substituted by methyl, hydroxy, halogen or amino. It is also preferred that X should be nitro or cyano and Y should be hydrogen. Particularly useful compounds are:

1-nitro-2-methylamino-2-[2-(4-methyl-5-imidazolylmethylthio)ethylamino]ethylene,
1-nitro-2-methylamino-2-[2-(3-bromo-2-pyridyl methylthio)ethylamino]ethylene,
1-nitro-2,2-bis[2-(4-methyl-5-imidazolylmethylthio)ethylamino]ethylene,
1-nitro-2,2-bis-[2-(3-bromo-2-pyridylmethylthio)ethylamino]ethylene,
1-nitro-2-methylamino-2-[(2-thiazolylmethylthio)ethylamino]ethylene and
1-nitro-2,2-bis-[2-(2-thiazolylmethylthio)ethylamino]ethylene A general method for the preparation of the compounds of the present invention is shown in the following Scheme 1:

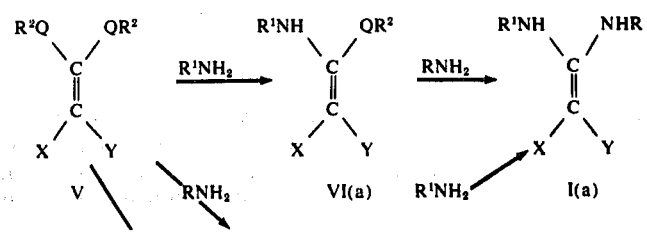

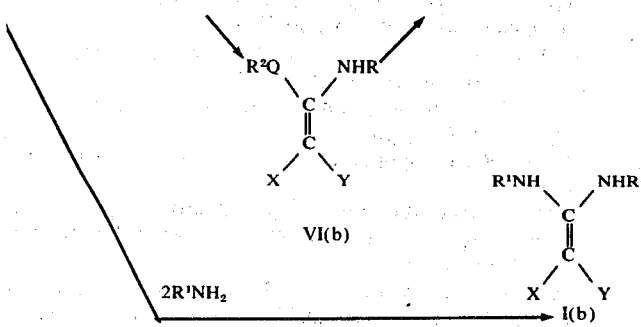

SCHEME 1

The starting material is a compound of Formula V wherein Q is sulphur or oxygen, preferably sulphur, and R² is lower alkyl such as methyl, or aralkyl, such as benzyl, but is preferably methyl. This may be reacted with one equivalent of R¹ NH₂ or of RNH₂, R¹ and R have the same significance as in Formula I, to give respectively the compounds of Formulae VI(a) or VI(b) and then reacted with RNH₂ or R¹NH₂ respectively to give the compound of Formula I(a). In the case wherein R is the same as R¹ the reaction may be carried out in a single step by reacting the compound of Formula V with two equivalents of R¹NH₂ to give the product of Formula I(b). The reactions described in Scheme 1 may be carried out in a suitable solvent or, particularly when R is the same as R¹ in the absence of a solvent at a moderately elevated temperature, for example at from 90°–150°C.

The intermediate of Formula V wherein Q is sulphur (see Formula V(a) in the following Scheme 2):

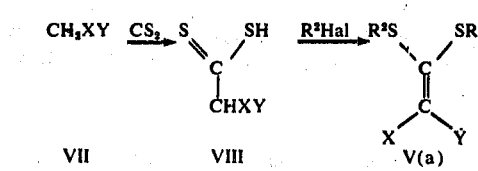

SCHEME 2 may be formed from the substituted methane of Formula VII by treatment of the latter with a strong base such as sodium hydride or sodium hydroxide and reaction with carbon disulphide to give the compound of Formula VIII. Treatment of this substance with an alkyl or aralkyl halide of Formulaa R² Hal gives the required compound of Formula V(a).

An alternative method for the preparation of the compounds of Formula I(a) is shown in Scheme 3.

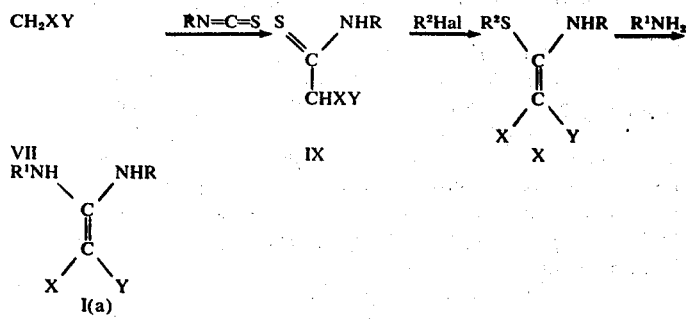

SCHEME 3

The substituted methane of Formula VII, after treatment with a strong base such as sodium hydride or sodium hydroxide, may be reacted with an isothiocyanate ester of Formula RN=C=S wherein R is lower alkyl to give the compound of Formula IX and reaction of this with the alkyl or aralkyl halide of Formula R² Hal results in the compound of Formula X wherein R is lower alkyl. Further reaction of the compound of Formula X with an amine of Formula R¹NH₂ yields the required compound of Formula I(a).

A further method which may be used in the preparation compounds wherein R is hydrogen, X is SO₂Ar and Y is hydrogen (Formula I(c)) is shown in Scheme 4:

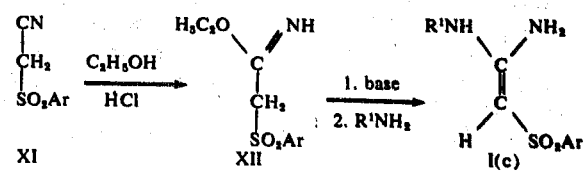

SCHEME 4

The arylsulphonylacetonitrile of Formula XI wherein Ar has the same significance as in Formula I is reacted under anhydrous conditions with ethanol and hydrogen chloride to give the iminoether of Formula XII. Treatment of this with a base and subsequent reaction with an amine of Formula R¹NH₂ gives the required product of Formula I (c).

It will be appreciated that the final stage of the reactions shown in Scheme 1, 3 and 4 may all be expressed by the following reaction:

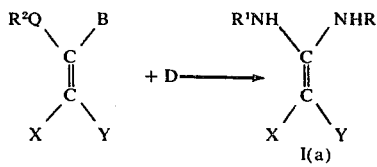

wherein B is RNH or R¹NH; D is R¹NH₂ or RNH₂; X, Y, R and R¹ have the same significance as in Formula I(a) and Q and R² have the same significance as in Formula V, provided that, when B is RNH, D must be R¹NH₂.

As stated above, the compounds represented by Formula 1 have been found to have pharmacological activity in the animal body as antagonists to certain actions of histamine which are not blocked by "antihistamines" such as mepyramine. For example they have been found to inhibit selectively the histamine-stimulated secretion of gastric acid from the perfused stomachs of rats anaesthetised with urethane at doses of from 0.5 to 256 micromoles per kilogram intravenously. Similarly, the action of these compounds is demonstrated by their antagonism to the effects of histamine on other tissues which, according to the above-mentioned paper of Black et. al., are H-2 receptors. Examples of such tissues are perfused isolated guinea-pig atrium and isolated rat uterus. The compounds of the invention have also been found to inhibit the secretion of gastric acid stimulated by pentagastrin or by food.

The level of activity found for the compounds of the present invention is illustrated by the effective dose range in the anaesthetised rat, as mentioned above of from 0.5 to 256 micromoles per kilogram, intravenously. Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefore. Such addition salts include those with hydrochloric, hydrobromic, hydriodic, sulphuric and maleic acids and may conveniently be formed from the corresponding bases of formula I by standard procedures, for example by treating the base with an acid in a lower alkanol.

Pharmaceutical compositions comprising a pharmaceutical carrier and a compound of formula I or a pharmaceutically acceptable acid addition salt thereof and methods of inhibiting H-2 histamine receptors which comprise administering a compound of formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg to about 250 mg, most preferably from about 100 mg to about 200 mg.

The active ingredient will preferably be administered in equal doses one to three times per day. The daily dosage regimen will preferably be from about 150 mg to about 750 mg, most preferably from about 300 mg to about 600 mg.

Other pharmacologically active compounds may in certain cases be included in the composition. Advantageously the composition will be made up in a dosage unit form appropriate to the desired mode of administration, for example as a tablet, capsule or injectable solution. The invention is illustrated but in no way limited by the following Examples:

EXAMPLE 1

1,1-Dicyano-2-methylamino-2-[2-((4-methyl-5-imidazolyl)methylthio)ethylamino]ethylene.

Method (a)

i. Sodium hydride (50% oil dispersion, 9.6 g) was added portionwise to a solution of malononitrile (13.21 g) in dry dimethylformamide (150 ml). The mixture was stirred at 0° for 10 minutes and then to it was added dropwise a solution of methyl isothiocyanate (14.62 g) in dimethylformamide, maintaining the reaction temperature below 40°. The dark red solution was stirred for 45 minutes and a solution of methyl iodide (28.4 g) in dimethylformamide (25 ml) was then added. The reaction mixture was stirred vigorously for 20 minutes and then poured on to crushed ice (500 ml). The crude product (26 g, m.p. 115°) was filtered off and taken up in hot ethanol-ether (3:1, 600 ml). Filtration and cooling furnished 1,1-dicyano-2-methylthio-2-methylamino ethylene m.p. 119°–120°. Further recrystallisation from water gave a sample of m.p. 120°–121°.

(Found: C, 46.7; H, 4.6; N, 27.1; S, 20.8. $C_6H_7N_3S$ requires: C, 47.0; H, 4.4; N, 27.4; S, 20.9)

ii. To a stirred suspension of 4-methyl-5-[2-aminoethyl)thiomethyl]imidazole (1.71 g) in dry acetonitrile (30 ml) was added, 1,1-dicyano-2-methylthio-2-methylamino ethylene (1.53 g). The mixture was stirred at room temperature for one hour and the crude product (1.36 g) was collected. Recrystallisation from boiling water furnished 1,1-dicyano-2-methylamino-2-

[2-((4-methyl-5-imidazolyl)methylthio)ethylamino]ethylene, m.p. 133°–135°.

(Found C, 52.4; H, 5.8; N, 30.5; S, 11.6; $C_{12}H_{16}N_6S$ requires: C, 52.2; H, 5.8; N, 30.4; S, 11.6).

Method (b)

A mixture of 1,1-dicyano-2-ethoxy-2-methylaminoethylene (2.27 g) and 4-methyl-5-[(2-aminoethyl)thiomethyl]imidazole (2.57 g) in acetonitrile (25 ml) was stirred at room temperature for 23 hours. The reaction mixture was then evaporated to dryness and the residual oil chromatographed on silica gel using acetone as eluent to give, after removal of the solvent, 1,1-dicyano-2-methylamino-2-[2-((4-methyl-5-imidazolyl)methylthio)ethylamino]ethylene, m.p. 131°–133°.

EXAMPLE 2

1-Nitro-2-methylamino-2-[2-(4-methyl-5-imidazolyl)methylthio)ethylamino]ethylene i. A solution of 4-methyl-5-[(2-aminoethyl)thiomethyl]imidazole (1.71 g) in t-butanol (30 ml) was added slowly to a solution of 1-nitro-2,2-bis methylthioethylene (1.66 g) in acetonitrile (20 ml) at room temperature. The solution heated under reflux for 3 hours, evaporated to dryness and chromatographed on a column of silica gel with elution by anhydrous ether (250 ml) followed by acetone (500 ml). The acetone eluate was concentrated to low bulk to give 1-nitro-2-methylthio-2-[2-(4-methyl-5-imidazolyl)methylthio)ethylamino]ethylene (1.58 g), m.p. 151°–153°. A sample recrystallised from acetonitrile had m.p. 152°–153°.

(Found: C, 41.4; H, 5.3; N, 194.; S, 21.8; $C_{10}H_{16}N_4O_2S_2$ requires: C, 41.7; H, 5.6; N, 19.4; S, 22.2).

ii. A mixture of 1-nitro-2-methylthio-2[2-(4-methyl-5-imidazolyl)methylthio)ethylamino]ethylene (0.67 g) and 33% ethanolic methylamine (4 ml) was heated in a sealed tube at 70°–80° for 1 hour. Concentration, followed by purification of the product by chromatography on a column of silica gel with acetone as eluant and recrystallisation from acetonitrile furnished 1-nitro-2-methylamino-2-[2-((4-5-imidazolyl)methylthio)ethylamino]ethylene (0.39 g), m.p. 141–3°. Further recrystallisation from isopropanol furnished a sample m.p. 148°–151°.

(Found: C, 44.5; H, 6.6; N, 25.9; S, 11.4; $C_{10}H_{17}N_5O_2S$ requires: C, 44.3; H, 6.3; N, 25.8; S, 11.8).

EXAMPLE 3

1-Nitro-2-methylamino-2-[2-(2-pyridylmethylthio)ethylamino]ethylene i. A solution of 2-[(2-aminoethyl)thiomethyl]pyridine (5.0 g) and 1-nitro-2,2-bis-methylthioethylene (5.28 g) in ethanol was heated under reflux for 3 hours. Concentration and chromatographic purification of the product on a column of silica gel with elution by iso-propyl alcohol-ethylacetate (1:5) gave 1-nitro-2-methylthio-2-[2-(2-pyridylmethylthio)ethylamino]ethylene (2.49g), m.p. 95.5°–96.5°.

ii. A solution of the methylthio compound (2.4 g) in ethanolic methylamine (33% w/v 25 ml) was set aside overnight at room temperature. A crystalline solid was deposited which was collected and recrystallised from ethanol-ether to give the title compound (1.7 g), m.p. 112°–113°.

(Found: C, 49.5; H, 6.0; N, 20.9; S, 11.8?. $C_{11}H_{16}N_4O_2S$ requires: C, 49.4; H, 5.7; N, 21.0; S, 12.0).

EXAMPLE 4

1-Nitro-2-methylamino-2-[2-(3-bromo-2-pyridylmethylthio)ethylamino]ethylene i. A solution of 2-[(2-aminoethyl)thiomethyl]-3-bromopyridine (from the dihydrobromide, 3.0 g) and 1-nitro-2,2-bis-methyl thioethylene (1.21 g) in acetonitrile (30 ml) was set aside at room temperature for 3 days. The product was chromatographed on a column of silica gel with elution by ethyl acetate, to give 1-nitro-2-methylthio-2-[2-(3-bromo-2-pyridylmethylthio)ethylamino]ethylene (1.2 g), m.p. 79°–80° (from ethanol-ether).

(Found: C,36.3; H,3.9; N,11.5% $C_{11}N_{14}BrN_3O_2S_2$ requires: C, 36.3; H, 3.9; N, 11.5%).

ii. A solution of the methylthio compound (1.3 g) in ethanolic methylamine (33% w/v, 20 ml) was set aside overnight at room temperature and heated under reflux for 15 min. Cooling and dilution with ether yielded the title compound (1.3 g), m.p. 153°–154° (from ethanol).

(Found: C,38.6; H,4.5; N,16.8; S,9.7%). $C_{11}N_{15}BrN_4O_2S$ requires: C, 38.1; N, 4.4; N, 16.1; S, 9.2%).

EXAMPLE 5

1-Nitro-2,2-bis[2-(4-methyl-5-imidazolylmethylthio)ethylamino]ethylene

A mixture of 4-methyl-5-[(2-aminoethyl)thiomethyl]imidazole (6.82 g) and 1-nitro-2,2 - bis-methylthio ethylene (3.30 g) was heated at 140° for 2 hours. The product was chromatographed on a column of silica gel with elution by ethanol-ethylacetate (1:4) to separate 1-nitro-2-methylthio-2-[2-(4-methyl-5-imidazolyl) methylthio)ethylamino]ethylene (0.56 g, m.p. 150°–151° from ethanol-ether) and further elution by ethanol-ethyl acetate (3:2) to separate the title compound (6.5 g, m.p. 152°–153° from ethanol-ether).

(Found: C,46.5; H,6.1; N, 23.6; S,15.5%; $C_{16}H_{25}N_7O_2S_2$ requires: C, 46.7; H, 6.1; N, 23.8; S, 15.5%).

EXAMPLE 6

1-Nitro-2,2-bis-[2-(2-pyridylmethylthio)ethylamino]ethylene

A mixture of 2-[(2-aminoethyl)thiomethyl]pyridine (5.0 g) and 1-nitro-2, 2-bis-methylthio ethylene (2.64 g) was heated at 100° for 2 hours. The product was chromatographed on a column of silica gel with elution by iso-propylalcohol-ethyl acetate (1:10) to separate 1-nitro-2-methylthio-2-[2-(2-pyridyl methylthio)ethylamino]ethylene (0.3 g) and further elution by iso-propyl alcohol - ethylacetate (3:5) to separate the title compound (5.1 g, m.p. 86°–87°, from ethanol-ether).

(Found: C, 53.6; H, 5.6; N, 17.3; S, 15.6%. $C_{18}H_{23}N_5O_2S_2$ requires: C, 53.3; H, 5.7; N, 17.3; S, 15.8%.

EXAMPLE 7

1-Nitro-2,2-bis-[2-(3-bromo-2-pyridylmethyl thio)ethylamino]ethylene

A mixture of 2-[(2-aminoethyl)thiomethyl]3-bromopyridine (3.0 g) and 1-nitro-2,2-bis-methylthioe thylene (1.0 g) was heated at 100° for 1 hour. The product crystallised from ethanol and recrystallisation from the same solvent afforded the title compound (2.1 g, m.p. 122°–123°C).

(Found: C, 38.2; H, 3.8; N, 12.4; S, 11.2 %. $C_{18}N_{21}Br_2N_5O_2S_2$ requires: C, 38.4; N, 3.8; N, 12.4; S,11.4%)

EXAMPLE 8

1-Benzenesulphonyl-2-amino-[2-(4-methyl-5-imidazolyl)methylthio)ethylamino]ethylene dihydrochloride Phenylsulphonyl acetonitrile (14.5 g) was suspended in anhydrous ether (100 ml) containing absolute ethanol (3.0 g) and into the stirred suspension was passed hydrogen chloride with stirring to a weight gain of 6.0 grams. Stirring was continued in the cold for 24 hours and the reaction mixture was then set aside in the cold for 3 days. The crystalline iminoether hydrochloride (13.4g) m.p. 148°–9° was collected. A solution of this hydrochloride (6.82 g) in aqueous potassium carbonate was extracted with ether and the ether extracts dried and concentrated which gave the imino ether as the free base. This was dissolved in acetonitrile (50 ml) containing 4-methyl-5-[(2-aminoethyl) thiomethyl-]imidazole (5.1 g) and the solution was left at room temperature for 24 hours, heated at 50° for 5 hours and finally heated at reflux for 1 hour. The product was chromatographed on a column of neutral alumina with elution by ethanol-ethyl acetate (3:2). The eluate was converted into a picrate which was recrystallised from nitromethane to afford the title compound as the dipicrate m.p. 175°–177°.

(Found: C, 39.8; H, 3.2; N, 17.5; S, 7.9% $C_{15}H_{20}N_4O_2S_2 2C_6H_3N_3O_7$ requires: C,40.0; H,3.2; N,17.3; S,7.9%). The dipicrate (0.5 g) was dissolved in aqueous methanol (1:1, 50 ml) and ion-exchanged to chloride on a column (IRA 401) in the Cl⁻ form. The eluate was lyophilised and dissolved in water to provide an aqueous solution of the title compound dihydrochloride (Found: Cl, 16.4% $C_{15}H_{20}N_4O_2S_2$ 2HCl requires: Cl, 16.7%)

EXAMPLE 9

2-Amino-1,1-dicyano-2[2-(4-methyl-5-imidazolyl)methylthio)ethylamino]ethylene

A solution of 4-methyl-5-[(2-aminoethyl) thiomethyl]imidazole (4.1 g) and 2-amino-1,1,-dicyano-2-methylthioethylene (2.3 g) in ethanol was heated under reflux for 2.5 hours. Concentration, followed by chromatographic purification on a column of silica gel with ethyl acetate as eluent afforded the title compound (1.32 g), m.p. 187°–188°.

(Found: C,50.2; H,5.4; N,31.6; S,11.7% $C_{11}H_{14}N_4S_6$ requires: C, 50.4; H,5.4; N,32.0; S,11.2%).

EXAMPLE 10

1-Nitro-2-ethylamino-2-[2-(4-methyl-5-imidazolyl)-methylthio]ethylamino ethylene Reaction of 1-nitro-2-methylthio-2[2-((4-methyl-5-imidazolyl)methylthio)ethylamino]ethylene with ethylamine according to the process of Example 2(ii) yielded the title compound, m.p. 171°–172°.

(Found: C,46.2; H,6.7; N,24.3; S,11.0%. $C_{11}H_{19}H_5O_2S$ requires: C,46.3; H,6.7; N,24.5; S,11.2%).

EXAMPLE 11

1-Nitro-2-methylamino-2-[(2-thiazolylmethylthio)ethylamino]ethylene i. By the procedure of Example 4(i), 2-[(2-aminoethyl)thiomethyl]thiazole (from the dihydrobromide, 4.0g) is reacted with 1-nitro-2,2-bis methylthioethylene (2.0g) to give 1-nitro-2-methylthio-2-[(2-thiazolymethylthio)ethylamino]ethylene, m.p. 63°–64°.

ii. Reaction of 1-nitro-2-methylthio-2-[(2-thiazolylmethylthio)ethylamino]ethylene with methylamine according to the process of Example 3 (ii) yielded the title compound, m.p. 103°–104°(from ethanol ether).

(Found: C,39.4; H,5.2; N,20.2% $C_9H_{14}N_4O_2S_2$ requires: C,39.4; H,5.1; N,20.4%).

EXAMPLE 12

1-Nitro-2,2-bis-[2-(2-thiazolylmethylthio)ethylamino]ethylene

Reaction of 2-[(2-aminoethyl)thiomethyl]thiazole (from the dihydrobromide 4.0g) with 1-nitro-2,2-bis-methylthioethylene (0.99g) according to the precedure of Example 6 yielded the title compound, m.p. 50°–51° (from ethanol-ether).

(Found: C,39.6; H,4.6; N,16.4%. $C_{14}H_{19}N_5O_2S_4$ requires: C,40.2; H,4.6; N,16.8%).

EXAMPLE 13

1-Cyano-2-methylamino-2-[2-(4-methyl-5-imidazolyl methylthio)ethylamino]ethylene 4-Methyl-5-[(2-aminoethyl)thiomethyl]imidazole (3.5g) was added to a solution of 1-cyano-2-ethoxy-2-methylaminoethylene (3.1g) and the solution was stirred for 5 hours at 100°. The product was chromatographed on a column of neutral alumina with elution bychloroform/ethyl acetate (1:1) to give the title compound as a glass.

The NMR spectrum in CDCl₃, recorded at 60 mHz showed the following resonances:

| | | |
|---|---|---|
| imidazole-2-H; | singlet at δ7.46 | integral 1.2 protons; calculated, 1.0 protons. |
| imidazole-CH₃; | singlet at δ 3.71 | integral 2.0 protons; calculated 2.0 protons. |
| S—CH₂—CH₂—N; | multiplet at 187–215 H, | integral 2.4 protons |
| vinylic-H; | singlet at δ2.85 | integral 6.07 protons; calculated 6.0 protons |
| S—CH₂—CH₂—N; | multiplet 145–183 H, | |
| —NHCH₃; | singlet at δ2.77 | |
| CH₃-imidazole; | singlet at δ2.2 | The integral was used as the internal standard equal to 3.0 protons. |

EXAMPLE 14

1-Nitro-2-methylamino-2-[4-(4-imidazolyl)-butylamino]ethylene

Reaction of 4-(4-aminobutyl)imidazole (from the dihydrobromide (3.6g) with 1-nitro-2,2-bis-methylthioethylene (2.0g) by the procedure of Example 4(i) and treatment of the resultant 1-nitro-2-methylthio-2-[4-(4-imidazolyl)butylamino]ethylene with methylamine according to the procedure of Example 3(ii) gives the title compound.

EXAMPLE 15

1-Nitro-2-methylamino-2-[3-(2-imidazolythio)-propylamino]ethylene

By the procedure of Example 4(i), 2-(3-aminopropylthio)imidazole (from the dihydrobromide (3.8 g)) is reacted with 1-nitro-2,2-bis-methylthioethylene (2.0 g) to give 1-nitro-2-methylthio-2-[3-(2-imidazolythio)propylamino]ethylene which, on treatment with methylamine according to the procedure of Example 3(ii) gives the title compound.

EXAMPLE 16

1-Nitro-2-methylamino-2-[2-(2-(4-imidazolyl)ethylthio)ethylamino]ethylene

4-[2-(2-Aminoethylthio)ethyl]imidazole (from the dihydrobromide (4.0 g)) is reacted with 1-nitro-2,2-bis-methylthioethylene (2.0 g) by the procedure of Example 4(i) and the resultant 1-nitro-2-methylthio-2-[2-(2-(4-imidazolyl)ethylthio)ethylamino]ethylene is treated with methylamine according to the procedure of Example 3(ii) to yield the title compound.

EXAMPLE 17

When 4-bromo-5-[(2-aminoethyl)thiomethyl]imidazole (from the dihydrobromide (4.8 g)) is reacted with 1-nitro-2,2-bis-methylthioethylene (2.0 g) according to the procedure of Example 4(i) and the resultant 1-nitro-2-methylthio-2- 2-((4-bromo-5-imidazolyl)methylthio)ethylamino ethylene treated with methylamine by the procedure of Example 3(ii) there is produced 1-nitro-2-methylamino-2-[2-((4-bromo-5-imidazolyl)methylthio)ethylamino]ethylene.

When 3-[(2-aminoethyl)thiomethyl]isothiazole or 4-bromo-3-[2-aminoethyl)thiomethyl]isothiazole are used as the starting materials in the above process, the products are, respectively, 1-nitro-2-methylamino-2-[2-(3-isothiazolylmethylthio)ethylamino]ethylene and 1-nitro-2-methylamino-2-[2-((4-bromo-3-isothiazolyl)methylthio)ethylamino]ethylene.

EXAMPLE 18

By the procedure of Example 4(i), 3-hydroxy-2-[(2-aminoethyl)thiomethyl]pyridine (from the dihydrobromide (4.2 g)) is reacted with 1-nitro-2,2-bis-methylthioethylene (2.0 g) to give 1-nitro-2-methylthio- 2-[2-((3-hydroxy-2-pyridyl)methylthio)ethylamino]ethylene which, on reaction with methylamine by the process of Example 3(ii) gives 1-nitro-2-methylamino-2-[2-((3-hydroxy-2-pyridyl)methylthio)ethylamino]ethylene.

When 3-amino-2-[(2-aminoethyl)thiomethyl]pyridine and 2-(3-aminopropylthio)oxazole are used as starting materials in the above procedure the products are, respectively, 1-nitro-2-methylamino-2-[2-((3-amino-2-pyridyl)methylthio)ethylamino]ethylene and 1-nitro-2-methylamino-2-[3-(2-oxazolylthio)-propylamino]ethylene.

EXAMPLE 19

Reaction of 3-[(2-aminoethyl)thiomethyl]isoxazole (from the dihydrobromide (3.8 g)) with 1-nitro-2,2-bis-methylthioethylene (2.0 g) by the procedure of Example 4(i) and treatment of the resultant 1-nitro-2-methylthio-2-[2-(3-isoxazolylmethylthio)ethylamino]ethylene with methylamine according to the procedure of Example 3(ii) gives 1-nitro-2-methylamino-2-[2-(3-isoxazolylmethylthio)ethylamino]ethylene.

Using 3-[(2-aminoethyl)thiomethyl]-1,2,4-triazole and 2-amino-5-[(2-aminoethyl)thiomethyl]-1,3,4-thiadiazole as the starting materials in the above process the products are, respectively 1-nitro-2-methylamino-2-[2-(3-(1,2,4-triazolyl)methylthio)ethylamino]ethylene and 1-nitro-2-methylamino-2[2-((2-amino-5-1,3,4-thiadiazolyl)methylthio)ethylamino]ethylene.

EXAMPLE 20

In the procedure of Example 8, replacement as starting material of phenylsulphonylacetonitrile by
 (4-chlorophenyl)sulphonylacetonitrile
 (3,4-dichlorophenyl)sulphonylacetonitrile
 (4-methylphenyl)sulphonylacetonitrile
 (4-aminophenyl)sulphonylacetonitrile
results in the formation of the following products:
 1-(4-chlorobenzene)sulphonyl-2-amino-[2-((4-methyl-5-imidazolyl)methylthio)ethylamino]ethylene
 1-(3,4-dichlorobenzene)sulphonyl-2-amino[2-((4-methyl-5imidazolyl)methylthio)ethylamino]ethylene
 1-(4-methylbenzene)sulphonyl-2-amino-[2-((4-methyl-5-imidazolyl)methylthio)ethylamino]ethylene
 1-(4-aminobenzene)sulphonyl-2-amino-[2-(4-methyl-5imidazolyl)methylthio)ethylamino]ethylene.

EXAMPLE 21

Reaction of 3-[(2-aminoethyl)thiomethyl]isothiazole with 1-nitro-2,2-bis-methylthioethylene according to the procedure of Example 6 yields 1-nitro-2,2-bis-[2-(3-isothiazolylmethylthio)ethylamino]ethylene.

EXAMPLE 22

By using diphenylsulphonylmethane as the starting material in place of malononitrile in the procedure of Example 1 (a)(i) there is produced 1,1-diphenylsulphonyl-2-methylthio-2-methylamino ethylene and when this is reacted with 4-methyl-5-[(2-aminoethyl)-thiomethyl]imidazole according to the procedure of Example 1 (a) (ii), the resultant product is 1,1-diphenylsulphonyl-2-methylamino-2-[2-((4-methyl-5-imidazolyl)methylthio)ethylamino]ethylene.
  By the same procedure, starting from
  dinitromethane,
  nitroacetonitrile,
  phenylsulphonylnitromethane and
  phenylsuphonylacetonitrile
the following products may be produced
  1,1-dinitro-2-methylamino-2-[2-((4-methyl-5-imidazolyl)methylthio)ethylamino]ethylene, 1-cyano-1-nitro-2-methylamino-2-[2-((4-methyl-5-imidazolyl)methylthio)ethylamino]ethylene, 1-nitro-1-phenylsulphonyl-2-methylamino-2-[2-((4-methyl-5-imidazolyl)methylthio)ethylamino]ethylene and 1-cyano-1-phenylsulphonyl-2-methylthio-2-[2-((4-methyl-5-imidazolyl)methylthio)ethylamino]ethylene.

EXAMPLE 23

Reaction of 1-nitro-2-methylthio-2-[2-((4-methyl-5-imidazolyl)methylthio)ethylamino]ethylene with an excess of 2-[(2-aminoethyl)thiomethyl]thiazole according to the procedure of Example 2 (ii) results in the production of 1-nitro-2-[2-((4-methyl-5-imidazolyl)methylthio)ethylamino]-2-[2-(2-thiazolylmethylthio)ethylamino]ethylene.

By the same procedure, reaction of 1-nitro-2-methylthio-2-[2-((4-methyl-5-imidazolyl)methylthio)ethylamino]ethylene with the following compounds 3-bromo-2-[(2-aminoethyl)thiomethyl]pyridine,
3-[(2-aminoethyl)thiomethyl]isothiazole,
4-(4-aminobutyl)imidazole and
4-bromo-5-[(2-aminoethyl)thiomethyl]imidazole yields respectively the products 1-nitro-2-[2-((4-methyl-5-imidazolyl)methylthio)ethylamino]2-[2-((3-bromo-2-pyridyl)methylthio)ethylamino]ethylene, 1-nitro-2-[2-((4-methyl-5-imidazolyl)methylthio)ethylamino]-2-[2-(3-isothiazolylmethylthio)ethylamino]ethylene, 1-nitro-2-[2-((4-methyl-5-imidazolyl)methylthio)ethylamino]-2-[4-(4-imidazolyl)butyl]ethylene and 1-nitro-2-[2-((4-methyl-5-imidazolyl)methylthio)ethylamino]-2-[2-((4-bromo-5-imidazolyl)methylthio)ethylamino]ethylene.

EXAMPLE 24

Reaction of 1-nitro-2-methylthio-2-[(2-thiazolylmethylthio)ethylamino]ethylene, produced by the process of Example 11 (i), with 3-bromo-2-[(2-aminoethyl)thiomethyl]pyridine and
3-[(2-aminoethyl)thiomethyl]isothiazole by the procedure of Example 2 (ii) results in the production of the following compounds 1-nitro-2-[2-(2-thiazolylmethylthio)ethylamino]-2-[2-((3-bromo-2-pyridyl)methylthio)ethylamino]ethylene and 1-nitro-2-[2-(2-thiazolylmethylthio)ethylamino]-2-[2-(3-isothiazolylmethylthio)ethylamino]ethylene.

EXAMPLE 25

| Ingredients | Amounts |
|---|---|
| 1-Nitro-2-methylamino-2-[2-(4-methyl-5-imidazolylmethylthio)ethylamino]ethylene | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 26

| Ingredients | Amounts |
|---|---|
| 1-Nitro-2,2-bis-[2-(4-methyl-5-imidazolylmethylthio)ethylamino]ethylene | 200 mg |
| Lactose | 100 mg |

The ingredients are screened, mixed and filled into a hard gelatin capsule.

What we claim is:

1. A compound of the formula

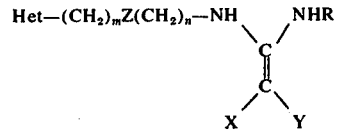

wherein X and Y, which may be the same or different, are hydrogen, nitro, cyano or $SO_2Ar$ but are not both hydrogen; R is hydrogen, lower alkyl or $Het(CH_2)_mZ(CH_2)_n$; Z is sulphur $m$ is 0, 1 or 2 and $n$ is 2 or 3, provided that the sum of $m$ and $n$ is 3 or 4; Het is a pyridine ring which ring is optionally substituted by lower alkyl, hydroxyl, halogen or amino; and Ar is an aryl group such as phenyl optionally substituted by halogen, methyl or amino or a pharmaceutically acceptable acid addition salt thereof.

2. A compound of claim 1 wherein X and Y are hydrogen, nitro or cyano; and R is hydrogen or lower alkyl.

3. A compound of claim 1 wherein R is methyl or Het $CH_2SCH_2CH_2$; $m$ is 1 and $n$ is 2.

4. A compound of claim 1 wherein Het is pyridine and is optionally substituted by methyl, hydroxy, halogen or amino.

5. A compound of claim 1 wherein X is nitro or cyano and Y is hydrogen.

6. A compound of claim 1, said compound being 1-nitro-2-methylamino-2-[2-((3-bromo-2-pyridyl)methylthio)ethylamino]ethylene.

7. A compound of claim 1, said claim being 1-nitro-2,2-bis-[2-((3-bromo-2-pyridyl)methylthio)ethylamino]ethylene.

* * * * *

UNITED STATES PATENT AND TRADEMARK OFFICE
CERTIFICATE OF CORRECTION

PATENT NO. : 3,953,460
DATED : April 27, 1976
INVENTOR(S) : Graham John Durant, John Colin Emmett, Charon Robin Ganellin and Hunter Douglas Prain It is certified that error appears in the above-identified patent and that said Letters Patent are hereby corrected as shown below:

Column 3, line 43, "VT(a)dor" should read -- VI(a) or --.

Column 7, line 43, "((4-5-" should read -- ((4-methyl-5- --.

Signed and Sealed this

Twenty-eighth Day of September 1976

[SEAL]

Attest:

RUTH C. MASON
Attesting Officer

C. MARSHALL DANN
Commissioner of Patents and Trademarks